US008858426B2

(12) United States Patent
Okuno

(10) Patent No.: US 8,858,426 B2
(45) Date of Patent: Oct. 14, 2014

(54) ULTRASOUND ENDOSCOPE SYSTEM AND CONTROL METHOD OF ULTRASOUND ENDOSCOPE SYSTEM

(75) Inventor: Yoshiyuki Okuno, Fussa (JP)

(73) Assignee: Olympus Medical Systems Corp., Tokyo (JP)

( * ) Notice: Subject to any disclaimer, the term of this patent is extended or adjusted under 35 U.S.C. 154(b) by 1529 days.

(21) Appl. No.: 12/050,318

(22) Filed: Mar. 18, 2008

(65) Prior Publication Data

US 2008/0249361 A1 Oct. 9, 2008

(30) Foreign Application Priority Data

Apr. 4, 2007 (JP) ................. 2007-098853

(51) Int. Cl.
*G06F 13/00* (2006.01)
*A61B 8/14* (2006.01)
*A61B 1/04* (2006.01)
*A61B 8/12* (2006.01)
*A61B 8/00* (2006.01)
*A61B 1/00* (2006.01)

(52) U.S. Cl.
CPC . *A61B 8/12* (2013.01); *A61B 8/585* (2013.01); *A61B 1/0005* (2013.01); *A61B 1/042* (2013.01); *A61B 8/467* (2013.01); *A61B 1/00039* (2013.01)
USPC ........... 600/118; 600/109; 600/462; 711/154; 711/156

(58) Field of Classification Search
USPC .......... 600/101, 109, 118, 437, 462; 700/250, 700/259, 2–5; 709/208, 211
See application file for complete search history.

(56) References Cited

U.S. PATENT DOCUMENTS

| 5,812,814 | A | * | 9/1998 | Sukegawa ................. 711/103 |
| 6,506,155 | B2 | | 1/2003 | Sluis |
| 2002/0175992 | A1 | * | 11/2002 | Eino ............................. 348/65 |
| 2006/0276687 | A1 | * | 12/2006 | Sato ............................ 600/118 |

FOREIGN PATENT DOCUMENTS

| EP | 1 728 463 A1 | 12/2006 |
| JP | 2001-350563 A | 12/2001 |
| JP | 2005-143582 * | 6/2005 ............... A61B 8/00 |
| JP | 2005-177348 | 7/2005 |
| WO | WO 2007/114085 A1 | 10/2007 |

* cited by examiner

*Primary Examiner* — Anhtuan T Nguyen
*Assistant Examiner* — Aaron B Fairchild
(74) *Attorney, Agent, or Firm* — Scully, Scott, Murphy & Presser, PC

(57) ABSTRACT

In the present invention, an ultrasound observation apparatus includes an information reposition portion; the information reposition portion is a storage portion for storing various state information in an endoscope processor inputted from a keyboard and is configured to include a memory controller and a data memory portion. Moreover, the keyboard is configured to include a key matrix, a keyboard controller, an ultrasound key processing portion and an endoscope key processing portion. This configuration allows the ultrasound observation apparatus to easily share various state information of a plurality of apparatuses making up the system.

4 Claims, 4 Drawing Sheets

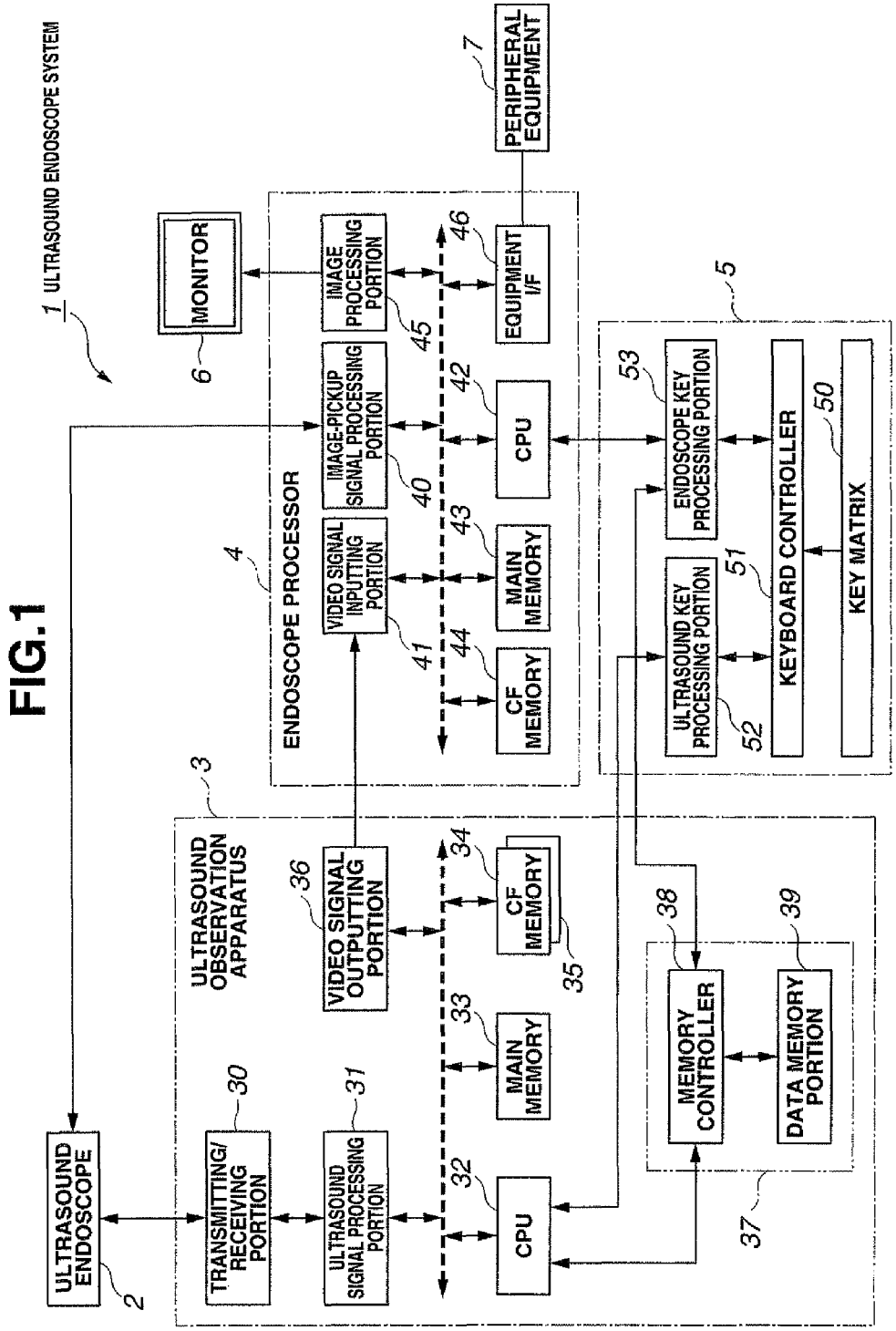

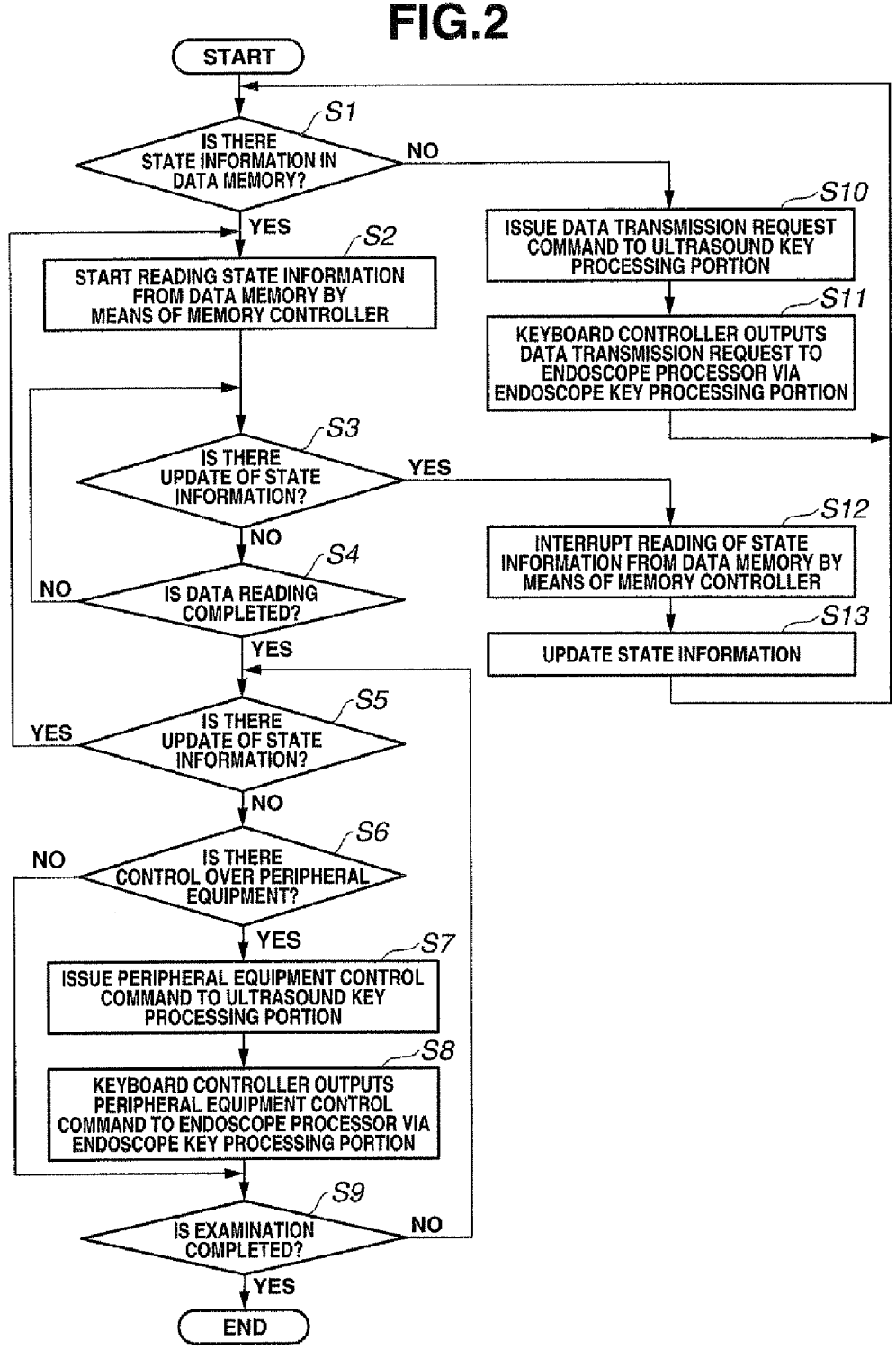

FIG.3

|  | BEFORE-READING | AFTER-READING |
|---|---|---|
| SETTING STATE INFORMATION READ-IN FLAG: Flag 1 | ON | OFF |
| OPERATION STATE INFORMATION READ-IN FLAG: Flag 2 | ON | OFF |

FIG.4

|  | ULTRASOUND ENDOSCOPE OPERATION PORTION SWITCH | | | |
|---|---|---|---|---|
|  | SWITCH 1 | SWITCH 2 | SWITCH 3 | SWITCH 4 |
| ULTRASOUND CONTROL MODE | ULTRASOUND FUNCTION 1 | ULTRASOUND FUNCTION 2 | ULTRASOUND FUNCTION 3 | ULTRASOUND FUNCTION 4 |
| ENDOSCOPE CONTROL MODE | ENDOSCOPE FUNCTION 1 | ENDOSCOPE FUNCTION 2 | ENDOSCOPE FUNCTION 3 | ENDOSCOPE FUNCTION 4 |

FIG.5

| ADDRESS | DATA | CONTENT OF DATA |
|---|---|---|
| 00 | 01234 | PATIENT ID |
| 01 | Ichiro Suzuki | PATIENT NAME |
| 02 | 28/Feb./1950 | DATE OF BIRTH |
| 03 | male | SEX |
| 04 | 2605L-1 | NAME OF ENDOSCOPE PROCESSOR |
| 05~ | : | IMAGE DATA |

ULTRASOUND ENDOSCOPE SYSTEM AND CONTROL METHOD OF ULTRASOUND ENDOSCOPE SYSTEM

CROSS REFERENCE TO RELATED APPLICATION

This application claims benefit of Japanese Patent Application No. 2007-098853 filed on Apr. 4, 2007, the contents of which are incorporated by this reference.

BACKGROUND OF THE INVENTION

1. Field of the Invention

The present invention relates to an ultrasound endoscope system and a control method of the ultrasound endoscope system, and more particularly to an ultrasound endoscope system made up of an ultrasound observation apparatus, an endoscope processor, and a keyboard connected to both the foregoing equipment, and a control method of the ultrasound endoscope system.

2. Description of the Related Art

In recent years, ultrasound endoscope systems which are made up of an ultrasound observation apparatus for endoscope (hereinafter abbreviated as an ultrasound observation apparatus), an endoscope processor, and a plurality of peripheral equipment connected to both the foregoing equipment are proposed in, for example, Japanese Patent Application Laid-Open No. 2005-143582, and Japanese Patent Application Laid-Open No. 2005-177348.

The ultrasound observation apparatus is configured to include a control circuit which causes an ultrasound tomography image (hereinafter, simply referred to as an ultrasound image) to be displayed on a display portion, the ultrasound image being obtained from a signal generated by performing a predetermined signal processing based on an ultrasound signal obtained by inserting an ultrasound endoscope, which is provided in the distal end portion with an ultrasound transducer, into a body cavity and driving the ultrasound transducer to transmit/receive an ultrasound, as well as controls the entire system.

The ultrasound endoscope is provided at the distal end of its insertion portion with an image pickup device etc.; the endoscope processor receives an image signal obtained by the ultrasound endoscope and subjects it to a predetermined signal processing to generate a signal, by which an endoscope image is displayed on the display portion.

Ultrasound diagnostic apparatus systems (or ultrasound endoscope systems), in which the above described two equipment are electrically connected with a plurality of peripheral equipment, for example, a printer (a video printer etc.), an information recording apparatus (an image file system etc.), an information inputting apparatus (a card reader etc.), and an operation instruction inputting apparatus (a keyboard etc.), have been commercialized and in widespread use.

Conventionally, after an ultrasound endoscope system is constructed by electrically connecting the ultrasound observation apparatus and the endoscope processor with respective peripheral equipment by using a connection cable; the setting etc. of the ultrasound observation apparatus and the endoscope processor, and the peripheral equipment connected thereto are all manually performed by a user or equipment administrator (hereinafter referred to as a user etc.) based on technical data (hereinafter simply referred to as an instruction manual etc.) such as an instruction manual, a sales manual, and a connection wiring diagram corresponding to each equipment.

On the other hand, some of conventional ultrasound endoscope systems are configured to include an operation instruction inputting apparatus such as a keyboard (hereinafter simply referred to as a keyboard) in order to convey an instruction signal etc. to the ultrasound observation apparatus and the endoscope processor. In some cases, the keyboard is electrically connected to the both equipment respectively: the ultrasound observation apparatus and the endoscope processor, so that one keyboard can be used in common for both the equipment.

The system of Japanese Patent Application Laid-Open No. 2005-143582 is an ultrasound diagnostic apparatus system made up of an ultrasound observation apparatus, an endoscope processor, and a plurality of peripheral equipment connected to both the foregoing equipment, the system being configured to include a system setting portion provided in any one of the ultrasound observation apparatus and the endoscope processor, a communication portion for transferring the information set by the system setting portion to the other of the ultrasound observation apparatus and the endoscope processor, and an operation setting modification portion for performing its own setting based on the system setting information transferred from the communication portion.

Further, the system of Japanese Patent Application Laid-Open No. 2005-177348 is an ultrasound diagnostic apparatus system made up of an ultrasound observation apparatus, an endoscope processor, and a plurality of peripheral equipment including an operation portion connected to both the foregoing equipment, wherein the ultrasound observation apparatus comprises a control circuit which comprises: a first storage portion for prestoring one or both of online manual information and help information relating to the system; a second storage portion for storing a usage situation of the system whenever necessary; and a selection portion for displaying information selected based on each information stored in the first storage portion and the second storage portion, on a display apparatus; and wherein the selection portion reads usage situation information stored in the second storage portion upon receiving an instruction signal from the operation portion, and reads information corresponding to the usage situation information from the first storage portion to transfer it to the display apparatus.

SUMMARY OF THE INVENTION

The ultrasound endoscope system of the present invention comprises:

an ultrasound endoscope which is inserted into a body cavity to acquire ultrasound data in the body cavity and optical image data in the body cavity;

an ultrasound observation apparatus for applying data processing to the ultrasound data to generate an ultrasound image;

an endoscope processor for applying data processing to the optical image data to generate an endoscope image;

an information inputting portion for inputting information to the ultrasound observation apparatus and the endoscope processor;

an information reposition portion which allows setting state information provided by the information inputting portion for one of the ultrasound observation apparatus and the endoscope processor to be written thereinto via the information inputting portion, as well as allows the written setting state information to be read therefrom at the other of the ultrasound observation apparatus and the endoscope processor; and an information reposition control portion for controlling the writing/reading of the information of the information reposition portion.

Other features and benefits of the present invention will be made clear by the following description.

BRIEF DESCRIPTION OF THE DRAWINGS

FIGS. 1 to 6 relate to embodiment 1 of the present invention, in which

FIG. 1 is a configuration diagram to show the configuration of an ultrasound endoscope system;

FIG. 2 is a flowchart to show the flow of processing in the ultrasound observation apparatus of FIG. 1;

FIG. 3 illustrates the flag of a memory controller in the processing of FIG. 2;

FIG. 4 illustrates the function of an operation switch provided in the ultrasound endoscope in the processing of FIG. 2;

FIG. 5 shows an example of the data format of the data file reposited in the information reposition portion of FIG. 1; and FIG. 6 is a configuration diagram to show the configuration of a variation of the ultrasound endoscope system of FIG. 1.

DETAILED DESCRIPTION OF THE PREFERRED EMBODIMENTS

Embodiment 1

Figure 6:
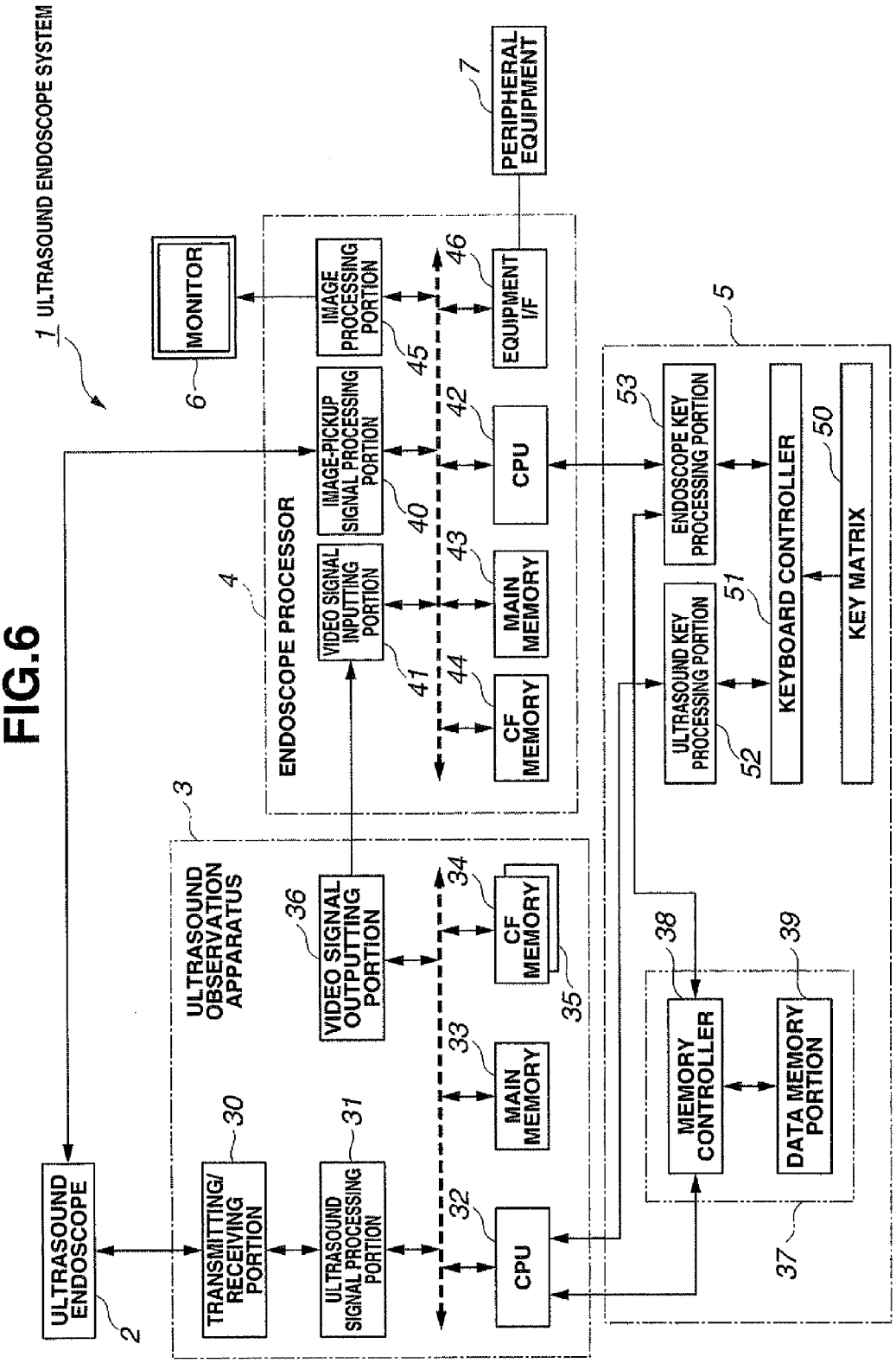

As shown in FIG. 1, an ultrasound endoscope system 1 is configured to include: an ultrasound endoscope 2 which is inserted into a body cavity to pick up an ultrasound echo signal and an image within the body cavity; an ultrasound observation apparatus 3 for driving an ultrasound device (not shown) of the ultrasound endoscope 2 and applying signal processing to the ultrasound echo signal to generate an ultrasound image; an endoscope processor 4 for driving an image pickup device (such as a CCD and a CMOS, not shown) of the ultrasound endoscope 2 and applying signal processing to an image pickup signal to generate an endoscope image; and a keyboard 5 for inputting various instruction signals to the ultrasound observation apparatus 3 and the endoscope processor 4.

The ultrasound observation apparatus 3 is configured to include a transmitting/receiving portion 30, an ultrasound signal processing portion 31, a CPU 32, a main memory 33, two Compact Flash (™) memories (CF memories) 34, 35, a video signal outputting portion 36, and an information reposition portion 37.

The transmitting/receiving portion 30 transmits a drive signal to the ultrasound device of the ultrasound endoscope 2 and receives an ultrasound echo signal from the ultrasound device.

The ultrasound signal processing portion 31 is a processing portion for generating the above described drive signal and generating various ultrasound images (such as a B mode image and a doppler image) from the ultrasound echo signal. Details thereof will be omitted because they are known.

The CPU 32 is a control portion for controlling the entire ultrasound observation apparatus 3 and is operated by a system program stored in the main memory 33.

The CF memory 34 is a storage portion for storing an application program activated by the CPU 32; and the CF memory 35 is a storage portion for storing an ultrasound image generated at the ultrasound signal processing portion 31.

The video signal outputting portion 36 outputs the ultrasound image generated at the ultrasound signal processing portion 31 or the ultrasound image stored in the CF memory 35, to the endoscope processor 4.

The information reposition portion 37 is a storage portion for storing various state information in the endoscope processor 4 inputted by the keyboard 5, and is configured to include a memory controller 38 as the information reposition control portion and a data memory portion 39 as the information reposition portion. The memory controller 38 manages the writing and reading at the data memory portion 39 and transmits/receives data to/from the CPU 32 and a later-described endoscope key processing portion 53 of the keyboard 5.

The endoscope processor 4 is configured to include an image-pickup signal processing portion 40, a video signal inputting portion 41, a CPU 42, a main memory 43, a CF memory 44, an image processing portion 45, and an equipment I/F portion 46.

The image-pickup signal processing portion 40 transmits a drive signal to the image pickup device of the ultrasound endoscope 2, receives an image pickup signal from the image pickup device, performs a predetermined signal processing on the received image pickup signal, and generates an endoscope image. Details thereof will be omitted because they are known.

The video signal inputting portion 41 is an inputting portion for inputting an ultrasound image from the video signal outputting portion 36 of the ultrasound observation apparatus 3.

The CPU 42 is a control portion for controlling the entire endoscope processor 4, and is operated by a system program stored in the main memory 43.

The CF memory 44 is a storage portion for storing endoscope images generated at the image-pickup signal processing portion 40 and ultrasound images inputted from the video signal inputting portion 41.

Moreover, ultrasound image data in real time is stored in the main memory 43. Further, the CF memory 44 is a memory for data saving connected via a card slot (not shown).

The image processing portion 45 is a processing portion for generating a display image in order to display the endoscope image and the ultrasound image stored in the CF memory 44 on a monitor 6.

The equipment I/F portion 46 is an interface for transmitting/receiving data to/from various peripheral equipment 7 such as a printer apparatus (a video printer) and an information recording apparatus (image filing apparatus).

The keyboard 5 is configured to include a key matrix 50, a keyboard controller 51, an ultrasound key processing portion 52 and an endoscope key processing portion 53.

The key matrix 50 is configured to include a group of switches made up of a plurality of switches for inputting data.

The keyboard controller 51 is a control portion for managing the operational state of the plurality of switches of the key matrix 50 and controlling the entire keyboard 5.

The ultrasound key processing portion 52 outputs the data inputted at the key matrix 50 to the CPU 32 of the ultrasound observation apparatus 3 based on the control by the keyboard controller 51 and outputs a control command from the CPU 32 of the ultrasound observation apparatus 3 to the keyboard controller 51. Here, the control command from the CPU 32 of the ultrasound observation apparatus 3, which is, for example, a command to perform recording to the peripheral equipment 7 as a recording target of ultrasound images, is transmitted to the CPU 42 of the endoscope processor 4 via the keyboard controller 51 and the endoscope key processing portion 53.

The endoscope key processing portion 53 outputs the data inputted at the key matrix 50 based on the control by the keyboard controller 51 to the CPU 42 of the endoscope processor 4 and the memory controller 38 of the ultrasound observation apparatus 3, as well as outputs the control command from the CPU 32 of the ultrasound observation apparatus 3 to the CPU 42 of the endoscope processor 4 through the keyboard controller 51.

Next, description will be made on the action of the present embodiment configured as so far described. When the ultrasound endoscope system 1 made up of the ultrasound observation apparatus 3 and the endoscope processor 4 is constructed, the keyboard controller 51 of the keyboard 5 controls the endoscope key processing portion 53. Then the endoscope key processing portion 53 outputs the data inputted at the key matrix 50 to the CPU 42 of the endoscope processor 4 and the memory controller 38 of the ultrasound observation apparatus 3 based on the control by the keyboard controller 51.

By this operation, the CPU 42 of the endoscope processor 4 recognizes patient information (information such as patient ID, patient name, patient age, and patient sex) as setting state information from the keyboard 5 and reposits the recognized patient information in the CF memory 44.

Simultaneously, the memory controller 38 of the ultrasound observation apparatus 3 inputs the patient information from the endoscope key processing portion 53 and reposits it in the data memory portion 39. Then, the memory controller 38 sets a setting state information read-in flag, Flag 1, which is a flag for the CPU 32 of the ultrasound observation apparatus 3, into an ON state which indicates a "before-reading" state (see FIG. 3).

Then, as shown in FIG. 2, the CPU 32 of the ultrasound observation apparatus 3 judges if there is before-reading state information (which has not been read) in the data memory portion 39 of the information reposition portion 37 through the setting state information read-in flag, Flag 1, at step S1.

The CPU 32 of the ultrasound observation apparatus 3 performs this judgment through the flags (Flag 1, Flag 2) as shown in FIG. 3, which are managed by the memory controller 38 of the information reposition portion 37. Flag 1 is a flag for managing the setting state information, and Flag 2 is a flag for managing the operation state information of the endoscope processor 4.

Specifically, the setting state information, which is patient information (patient's ID, name, age, sex, etc.) or state information of setting value information (image processing setting values such as luminance, contrast, etc.) inputted from the keyboard 5 to the endoscope processor 4, is inputted into the memory controller 38 via the endoscope key processing portion 53 to be reposited in the data memory portion 39. The above described Flag 1 is a flag for managing the reading of the reposited setting state information in the data memory portion 39.

Further, the operation state information, which is state information to show the control state at the endoscope processor 4 (for example, an allocation state of the operation switches of the ultrasound endoscope 2 as shown in FIG. 4, a connection state of peripheral equipment connected to the endoscope processor 4, and the like) is inputted into the memory controller 38 and reposited in the data memory portion 39. The above described Flag 2 is a flag for managing the reading of the reposited operation state information at the data memory portion 39.

If the CPU 32 of the ultrasound observation apparatus 3 judges that there is before-reading state information (which has not been read) in the data memory portion 39 of the information reposition portion 37 through the flag of the memory controller 38 (Flag 1, Flag 2: see FIG. 3), the CPU 32 of the ultrasound observation apparatus 3 starts the read processing of the before-reading state information from the data memory portion 39 by means of the memory controller 38 at step S2.

Then, the CPU 32 of the ultrasound observation apparatus 3 judges if there is an update of state information to the data memory portion 39 (an update of setting information at the keyboard 5 or an update of operation state at the endoscope processor 4) through the flag of the memory controller 38 (Flag 1, Flag 2: see FIG. 3) at step S3.

Then, when judging that there is no update of state information, the CPU 32 of the ultrasound observation apparatus 3 judges if the reading of data is completed at step S4, and repeats step S3 and step S4 until the reading of data is completed.

Upon completion of the reading of data, the CPU 32 of the ultrasound observation apparatus 3 again judges if there is an update of state information to the data memory portion 39 (an update of setting information at the keyboard 5 or an update of operation state at the endoscope processor 4) at step S5 through the flag of the memory controller 38 (Flag 1, Flag 2: see FIG. 3). When there is a data update, the process returns to step S2, and when there is no data update, advances to step S6.

The CPU 32 of the ultrasound observation apparatus 3 judges if there is control over the peripheral equipment 7 (for example, data recording control of ultrasound image etc. to an information recording apparatus (an image filing apparatus), which is the peripheral equipment 7) at the ultrasound observation apparatus 3 at step S6. When there is control over the peripheral equipment 7, the process advances to step S7, and when there is no control over the peripheral equipment 7, advances to step S9.

At step S7, the CPU 32 of the ultrasound observation apparatus 3 issues a control command for the peripheral equipment to the ultrasound key processing portion 52. Then, at step S8, the keyboard controller 51 inputs the control command through the ultrasound key processing portion 52, and farther outputs the control command to the CPU 42 of the endoscope processor 4 via the endoscope key processing portion 53.

Then, at step S9, until the examination at the ultrasound endoscope system 1 is completed, the CPU 32 of the ultrasound observation apparatus 3 repeats the processing of the above described step S5 to step S9.

Further, at step S1, when judging that there is no before-reading state information (which has not been read) in the data memory portion 39 of the information reposition portion 37, through the flag, Flag 1, the CPU 32 of the ultrasound observation apparatus 3 issues a data-transmission request command to the ultrasound key processing portion 52 at step S10.

Then, at step S11, the keyboard controller 51 inputs the data-transmission request command via the ultrasound key processing portion 52, and further outputs the data-transmission request command to the CPU 42 of the endoscope processor 4 via the endoscope key processing portion 53.

The data-transmission request command causes the CPU 42 of the endoscope processor 4 to output the state information, which has been requested via the endoscope key processing portion 53, to the CPU 32 of the ultrasound observation apparatus 3.

Further when the CPU 32 of the ultrasound observation apparatus 3 judges that there is an update of the state information (an update of setting information at the keyboard 5 or an update of operation state at the endoscope processor 4) for the data memory portion 39, through the flag (Flag 1, Flag 2: see FIG. 3) of the memory controller 38 at step S3, the process advances to step S12.

At step S12, the CPU 32 of the ultrasound observation apparatus 3 controls the memory controller 38 to interrupt the reading of the data memory portion. Then, the CPU 32 of the ultrasound observation apparatus 3 waits for an update of the state information, and the process returns to step S1.

As so far described, according to the present embodiment, since when setting state information including the patient information is inputted into the endoscope processor 4 with the keyboard 5, the setting state information is automatically reposited in the data memory portion 39 of the ultrasound observation apparatus 3, the CPU 32 of the ultrasound observation apparatus 3 can recognize the setting state information of the endoscope processor 4 reposited in the data memory portion 39 via the memory controller 38. That is, the ultrasound observation apparatus 3 can easily share the setting state information with the endoscope processor 4 without need of any operation.

The CPU 32 of the ultrasound observation apparatus 3 can recognize the operation state information of the endoscope processor 4 reposited in the data memory portion 39, and can transmit for example a control command for the peripheral equipment 7 to the CPU 42 of the endoscope processor 4 successively via the ultrasound key processing portion 52, the keyboard controller 51, and the endoscope key processing portion 53 of the keyboard 5, to control the peripheral equipment 7.

Since the CPU 32 of the ultrasound observation apparatus 3 can transmit such a control command to the CPU 42 of the endoscope processor 4 not through a predetermined protocol communication, but via the keyboard 5 based on the operation state information reposited in the data memory portion 39, the ultrasound observation apparatus 3 can easily control the peripheral equipment 7 without needing any communication sequence.

Moreover, the ultrasound endoscope 2 has a plurality of operation portion switches in the operation portion and as shown in FIG. 4, the functions of the plurality of operation portion switches are set by the operation mode of the ultrasound endoscope system 1.

Specifically, the functions of the plurality of operation portion switches are set by an endoscope control mode by the endoscope processor 4 and an ultrasound control mode by the ultrasound endoscope 2 based on the operation state information of the endoscope processor 4 and are stored in the data memory portion 39.

Then, in the endoscope control mode, the plurality of operation portion switches provide switches for each actuating endoscope function (such as a release function and a freeze function of endoscope image) under the control by the endoscope processor 4. Further, in the ultrasound control mode, the plurality of operation portion switches provide switches for each actuating the ultrasound function (such as a release function and a freeze function of ultrasound image) under the control by the endoscope processor 4. For example, a freeze operation of ultrasound image is enabled by a switch in the endoscope.

Here, the data format of the data file stored in the information reposition portion 37 is shown in FIG. 5. Since, as shown by the data format of FIG. 5, there is a unique name (for example, "2605L-1") of the endoscope processor 4 in the data file, even if the version of the data format is changed and the number and length of the shared data are changed corresponding to the connected endoscope processor, it is possible to cope with those changes while maintaining the compatibility of the data file.

Moreover, as shown in FIG. 1, the information reposition portion 37 is supposed to be provided in the ultrasound observation apparatus 3, but without being limited to that, the information reposition portion 37 may be provided in the keyboard 5 as shown in FIG. 6.

Furthermore, though not shown, configuration may be such that the information reposition portion 37 is provided in the endoscope processor 4, and the function of the ultrasound key processing portion 52 is replaced by the function of the endoscope key processing portion 53; for example, configuration may be such that various state information set in the ultrasound observation apparatus 3 via the ultrasound key processing portion 52 is shared by the endoscope processor 4 and the ultrasound observation apparatus 3 by means of the information reposition portion 37.

In the present invention, it is obvious that different embodiments in a wide range may be configured based on the present invention without being deviated from the spirit and scope of the present invention. The present invention will not be limited by particular embodiments thereof other than being limited by the appended claims.

What is claimed is:

1. An ultrasound endoscope system, comprising:
an ultrasound endoscope which is adapted to be inserted into a body cavity to acquire ultrasound data in the body cavity and optical image data in the body cavity;
an ultrasound observation apparatus comprising a first control portion, for applying data processing to the ultrasound data to generate an ultrasound image;
an endoscope processor comprising a second control portion, for applying data processing to the optical image data to generate an endoscope image;
an information inputting device for inputting information to the ultrasound observation apparatus and the endoscope processor;
an information reposition memory which allows repositing state information for one of the ultrasound observation apparatus and the endoscope processor inputted to the information inputting device, the state information including patient information, setting value information for the one of the ultrasound observation apparatus and the endoscope processor, and operation state information for the one of the ultrasound observation apparatus and the endoscope processor, which are shared by the other of the ultrasound observation apparatus and the endoscope processor; and
an information reposition controller for controlling the repositing of the state information in the information reposition memory, setting information that indicates the repositing to a predetermined value when at least one of the patient information, the setting value information, and the operation state information of the state information is reposited in the information reposition memory, and controlling reading of the reposited state information based on the predetermined value of the information that indicates the repositing in the other of the ultrasound observation apparatus and the endoscope processor in order to cause the first control portion or the second control portion to acquire the reposited state information,
wherein when the reposited state information in the information reposition memory includes no information which has not been read from the information reposition memory, the first control portion or the second control portion of the other requests the first control portion or the second control portion of the one to transmit the state information.

2. The ultrasound endoscope system according to claim 1, wherein the information inputting device inputs a control command for controlling the one of the ultrasound observation apparatus and the endoscope processor from the other of the ultrasound observation apparatus and the endoscope processor and outputs the inputted control command to the one of the ultrasound observation apparatus and the endoscope processor.

3. The ultrasound endoscope system according to claim 1, wherein the information inputting device is a keyboard.

4. The ultrasound endoscope system according to claim 1, wherein the information reposition controller automatically writes the state information into the information reposition memory in order to reposit the state information in the information reposition memory.

* * * * *